United States Patent [19]

Schoenwald et al.

[11] Patent Number: 5,225,424
[45] Date of Patent: Jul. 6, 1993

[54] METHAZOLAMIDE-DERIVED CARBONIC ANHYDRASE INHIBITORS

[75] Inventors: Ronald D. Schoenwald; Charles F. Barfknecht, both of Iowa City, Iowa

[73] Assignee: University of Iowa Research Foundation, Oakdale, Iowa

[21] Appl. No.: 964,199

[22] Filed: Oct. 21, 1992

[51] Int. Cl.$^5$ .................. A61K 31/41; C07D 285/135
[52] U.S. Cl. .................................... 514/363; 548/139
[58] Field of Search ..................... 548/139; 514/363

[56] References Cited

U.S. PATENT DOCUMENTS

| | | | |
|---|---|---|---|
| 4,483,864 | 11/1984 | Barfknecht et al. | 514/363 |
| 4,483,872 | 11/1984 | Barfknecht et al. | 514/603 |
| 4,623,664 | 11/1986 | Schoenwald et al. | 514/653 |
| 4,629,738 | 12/1986 | Barfknecht et al. | 514/603 |
| 4,636,515 | 1/1987 | Barfknecht et al. | 514/363 |
| 4,705,798 | 11/1987 | Schoenwald et al. | 514/374 |
| 4,820,737 | 4/1989 | Schoenwald et al. | 514/654 |
| 4,866,083 | 9/1989 | Schoenwald et al. | 514/374 |
| 4,968,718 | 11/1990 | Schoenwald et al. | 514/532 |
| 4,975,447 | 12/1990 | Schoenwald et al. | 514/367 |
| 4,975,448 | 12/1990 | Schoenwald et al. | 514/367 |
| 4,975,449 | 12/1990 | Schoenwald et al. | 514/367 |
| 5,095,026 | 3/1992 | Schoenwald et al. | 514/367 |
| 5,104,887 | 4/1992 | Schoenwald et al. | 514/367 |
| 5,157,044 | 10/1992 | Schoenwald et al. | 514/363 |

*Primary Examiner*—Mary C. Lee
*Assistant Examiner*—Lenora A. Miltenberger
*Attorney, Agent, or Firm*—Zarley, McKee, Thomte, Voorhees & Sease

[57] ABSTRACT

N-[5-(aminosulfonyl)-3-methyl-1,3,4-thiadiazol-2(3H)ylidene] -2-acetyloxyacetamide, commonly referred to as acetylhydroxymethazolamide and is a water soluble pharmacologically active carbonic anhydrase inhibitor.

8 Claims, No Drawings

METHAZOLAMIDE-DERIVED CARBONIC ANHYDRASE INHIBITORS

BACKGROUND OF THE INVENTION

This invention relates to carbonic anhydrase inhibitors which can be prescribed topically for treatment of glaucoma. Topical drugs are of course preferred in that they have less systemic side effects than orally administered carbonic anhydrase inhibitors.

While the search for a truly effective topical anhydrase inhibitor has been going on for some time, many compounds that so far have been developed are not highly effective as carbonic anhydrase inhibitors, or provide allergic response. The most effective active compound for use as a topical carbonic anhydrase inhibitor would be one which provides a surprisingly high level of carbonic anhydrase inhibition, while at the same time is water soluble to allow easy administration and corneal permeability and finally one that does not provide an allergic response to the patients.

Surprisingly, it has been found that certain lower alkyl esters of hydroxymethazolamide have an unusually high level of solubility, are surprisingly active carbonic anhydrase inhibitors and at the same time provide compounds with no significant allergic potential.

Accordingly, it is a primary object of the present invention to provide an effective carbonic anhydrase inhibitor which merges the three important characteristics in a single compound, namely, solubility, high demonstrated carbonic anhydrase inhibition effect, and no significant allergic response.

Another objective of the present invention is to provide a method for topical application of carbonic anhydrase inhibitors which provide outstanding potency, compounds which are easy to synthesize, and compounds which have no significant allergic response potential.

A yet further objective of the present invention is to provide compositions which achieve the simultaneous objectives of high level potency, solubility and no significant allergic response.

Another objective of the present invention is to provide a convenient synthesis method for the carbonic anhydrase inhibitors of the present invention.

The method and manner of accomplishing each of the above objectives as well as others will become apparent from the detailed description of the invention which follows hereinafter.

SUMMARY OF THE INVENTION

Compounds representing structural modification of the methazolamide molecule, alkyl esters of hydroxymethazolamide, particularly acetyl ester, are prepared. These compounds surprisingly are soluble, have a high potency for lowering intraocular pressure and provide no significant allergic response.

DETAILED DESCRIPTION OF THE INVENTION

Inhibition of carbonic anhydrase is one mechanism of action by which the production of aqueous humor can be limited within the eye. If aqueous humor production can be limited, this in turn can be used to control ocular hypertension. Carbonic anhydrase inhibitors can be administered orally to reduce intraocular pressure (IOP), but this route of administration is associated with systemic side effects due to the large doses required to attain therapeutically useful levels in the eye. Topical administration of carbonic anhydrase inhibitors directly to the eye has the advantage of minimizing or eliminating systemic side effects due to the smaller doses required, and the more direct access the drug has to the organ. However, a carbonic anhydrase inhibitor may not produce optimum therapeutic effects, and may not be adequately absorbed or distributed to the active site, or may cause ocular irritation or local side effects as a result of changes in the carbonic anhydrase inhibitor molecule necessary to achieve water solubility. Thus, in preparing carbonic anhydrase inhibitors, one must constantly balance the activity, that is the effectiveness at inhibiting carbonic anhydrase, against the local or side effects that may be caused by changes necessary in the molecule in order to make it water soluble. For example, many carbonic anhydrase inhibitors that have been patented in the past achieve water solubility due to the presence of a tertiary amine which is protonated at physiological pH. Less than optimal water solubility of the active carbonic anhydrase inhibitor is accompanied by enhanced lipophilic solubility which translates into greater penetration to the site of action. However, if optimal water solubility were obtained by protonation to the active carbonic anhydrase inhibitor, one would necessarily be faced with less lipophilic character and accordingly a decreased amount of drug reaching the site of action, due to the more difficult penetration of the cornea. The net result would be a less clinically effective agent.

The carbonic anhydrase inhibitor derivatives of hydroxymethazolamide of the following general formula:

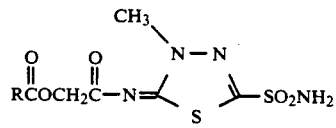

where R is $C_1$ to $C_8$. Preferably R is $C_1$ to $C_4$ are most preferably R is methyl.

The amount of active carbonic anhydrase inhibitor used in the composition should be from about 0.25% by weight to about 5% by weight of an eye drop test composition, preferably from about 0.5% by weight to about 2.0% by weight. The important point is not the dose amount, but simply that it be an effective carbonic anhydrase inhibiting amount, and yet not such a great amount that side effects will be achieved. Generally amounts within the range specified are satisfactory.

The diluent for the eye drop composition may be an isotonic eye treatment carrier buffered to a pH of from about 4.0 to about 8.0, and typically it will contain small amounts of conventional wetting agents and antibacterial agents. The preferred pH is within the range of from about 6.8 to about 7.8. Antibacterial agents, where they are included may be within the range of from about 0.004% by weight to about 0.02% by weight of the composition.

Compounds of the present invention, particularly acetylhydroxymethazolamide compound have potency levels at a range of approximately two to five-fold as much as most previously known carbonic anhydrase inhibitors given systemically. Moreover, they are also soluble.

Finally, initial screening with guinea pigs indicates no significant allergic potential. As an indication of level of potency, one of the more potent CAI compounds prepared to date is 6-aminobenzothiazolesulfonamide. It has a typical potency level of >30% reduction in IOP in high-pressure induced rabbit eyes. However, it has not achieved marketplace acceptance because of a significant allergic response. The present compound has a potency level of >34% reduction in IOP in the same rabbit assay, and demonstrates no significant allergic response. These are unexpected, superior results.

The following examples are offered to further illustrate but not limit the invention It goes without saying that certain minor modifications in structure of the molecules made herein may be made without departing from the spirit and scope of the invention and still achieve the objectives of the invention.

EXAMPLE 1

Synthesis of

N-[5-(aminosulfonyl)-3-methyl-1,3,4-thiadiazol-2(3H)-ylidene]-2-acetyloxyacetamide To a solution of 2-imino-3-methyl-1,3,4-thiadiazol-2(3H)ylidene]-5-sulfonamide [10 mmole]in dry pyridine [35 ml]was added acetoxyacetyl chloride [11.0 mmole]over a period of 15 minutes with stirring at −78° C. When the addition was completed, the reaction temperature was allowed to rise to room temperature while stirring was continued overnight. The reaction was quenched by the addition of 10 ml. water. The mixture was evaporated to dryness at reduced pressure. The solid product, which was recrystallized from 95% ethanol, had nuclear magnetic resonance spectra and a mass spectrum consistent with the assigned structure. The melting point analysis revealed a melting point within the range of from 138°–139° C.

EXAMPLE 2

Reduction in IOP following topical application of the compound of Example 1 to New Zealand White Rabbit Eyes The "IOP recovery rate assay" as reported by Vareilles and Lotti (Ophthal. Res., 13, 72–79, 1981) was used. In this assay 20% sodium chloride solution was infused into the marginal ear vein of New Zealand White rabbits for 10 minutes at a rate of 1 ml/min (n=10). IOP was measured at 15, 25, 35, 45, 60, 75, 90 and 120 minutes with an applanation pneumatonometer (Digilab Model D). Acetyl-hydroxymethazolamide (50 μL of a 2% solution containing a pH 8.0 phosphate buffer) was administered topically to the right eye 60 minutes before the start of the sodium chloride infusion. Control animals were given vehicle without drug.

The hypertonic sodium chloride solution causes a temporary decline in IOP which returns to normal IOP in about 90 minutes if no drug is administered. IOP gradually returns to normal at a constant rate but more slowly if a carbonic anhydrase inhibitor (CAI) is present at the active site (secretory cells located in the iris-ciliary body of the eye) in sufficient concentration. The return to normal IOP is measured from the positive linear slope which is a measure of the constant rate of return to normal IOP and begins at about 30–45 minutes after starting the NaCL infusion. A comparison of the slop with and without the addition of acetyl-hydroxymethazolamide to the rabbit eye is expressed as "% reduction".

RESULTS

The average (±standard deviation) slope values for 10 rabbit eyes was:
rabbit eye given vehicle only =0.085±0.031
rabbit eye given 2% acetyl-hydroxymethazolamide =0.056±0.018
% Reduction=34%

The results indicate that acetyl-hydroxymethazolamide is a potent in-vivo inhibitor of carbonic anhydrase.

What is claimed is:

1. A derivative of hydroxymethazolamide of the formula:

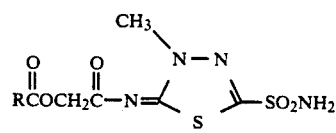

wherein R is $C_1$ to $C_8$ alkyl.

2. N-[5-(aminosulfonyl)-3-methyl-1,3,4-thiadiazol-2(3H)-ylidene]-2-acetyloxyacetamide.

3. A method of reducing intraocular eye pressure, said method comprising:
   a) topically applying to the eye a small but therapeutically effective intraocular eye pressure reducing amount of N-[5-(aminosulfonyl)-3-methyl-1,3,4-thiadiazol-2(3H)-ylidene]-2-acetyloxyacetamide having the formula:

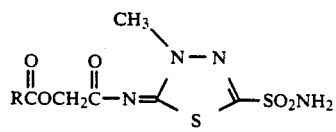

4. The method of claim 3 wherein the dose is from about 0.25% by weight to about 5% by weight of an eye drop composition.

5. The method of claim 4 wherein the dose is from about 0.5% by weight to about 2.0% by weight of an eye drop composition.

6. A topical composition for eye drop treatment comprising: a small but therapeutically effective intraocular eye pressure reducing amount of N-[5-(aminosulfonyl)-3-methyl-1,3,4-thiadiazol-2(3H)-ylidene]-2-acetyloxyacetamide of the formula:

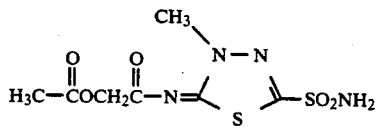

and, an ophthalmically acceptable carrier.

7. The composition of claim 6 wherein the amount of N-[5-(aminosulfonyl)-3-methyl-1,3,4-thiadiazol-2(3H)-ylidene]-2-acetyloxyacetamide is from 0.25% by weight of said composition to about 5.0% by weight of composition.

8. The composition of claim 7 wherein the amount of N-[5-(aminosulfonyl)-3-methyl-1,3,4-thiadiazol-2(3H)-ylidene]-2-acetyloxyacetamide is from about 0.5% by weight of said composition to about 2.0% by weight of said composition.

* * * * *